United States Patent [19]

McCullough

[11] Patent Number: 5,939,426
[45] Date of Patent: Aug. 17, 1999

[54] METHODS FOR TREATING URINARY INCONTINENCE USING DESCARBOETHOXYLORATADINE

[75] Inventor: John R. McCullough, Worcester, Mass.

[73] Assignee: Sepracor Inc., Marlborough, Mass.

[21] Appl. No.: 08/808,116

[22] Filed: Feb. 28, 1997

[51] Int. Cl.$^6$ .................................................. A61K 31/44
[52] U.S. Cl. ........................................................ 514/290
[58] Field of Search ............................................ 514/290

[56] References Cited

U.S. PATENT DOCUMENTS

| | | |
|---|---|---|
| 3,536,809 | 10/1970 | Applezweig . |
| 3,598,123 | 8/1971 | Zaffaroni . |
| 3,845,770 | 11/1974 | Theeuwes et al. . |
| 3,916,899 | 11/1975 | Theeuwes et al. . |
| 3,940,485 | 2/1976 | Levinson et al. ........................ 424/250 |
| 4,008,796 | 2/1977 | Aylon . |
| 4,282,233 | 8/1981 | Vilani . |
| 4,659,716 | 4/1987 | Villani et al. . |
| 4,777,170 | 10/1988 | Heinrich ................................ 514/226.2 |
| 5,595,997 | 1/1997 | Aberg et al. ............................ 514/290 |

FOREIGN PATENT DOCUMENTS

| | | |
|---|---|---|
| WO 92/20377 | 11/1992 | WIPO . |
| WO 96/20708 | 7/1996 | WIPO . |

OTHER PUBLICATIONS

Andersen and Feingold, 1995, "Adverse Drug Interactions Clinically Important for the Dermatologist", Arch. Dermatol. 131:468–473.

Berge, S. et al., 1977, "Pharmaceutical Salts", J. of Pharmaceutical Sciences 66:1–19.

Brandes, L. et al., 1992, "Stimulation of Malignant Growth in Rodents by Antidepressant Drugs at Clinically Relevant Doses", Cancer Research 52:3796–3800.

Brandes, L. et al., 1994, "Enhanced Cancer Growth in Mice Administered Daily Human–Equivalent Doses of Some $H_1$–Antihistamines: Predictive In Vitro Correlates", J. Nat'l. Cancer Institute 86:770–775.

Carmeliet, 1992, "Voltage– and Time–Dependent Block of the Delayed $K^+$ Current in Cardiac Myocytes by Dofetilide", J. Pharmocol. Exper. Ther. 262:809–817.

Cheung, B.S.K., et al., 1992, "Investigation of Anti–Motion Sickness Drugs in the Squirrel Monkey", J. Clin. Pharmacol. 32:163–175.

Clissold et al., 1989, "Loratadine: A Preliminary Reivew of its Pharmacodynamic Properties and Therapeutic Efficacy", Drugs 37:42–57.

Cohen, B. et al., 1972, "Meclizine and Placebo in Treating Vertigo of Vestibular Origin", Arch. Neurol. 27:129–137.

Cooke, R.D., 1983, "Glycopyrrolate in Bladder Dysfunction", S. Afr. Med. J. 63:3.

Craft, T., 1986, "Torsade de Pointes after Astemizole Overdose", British Medical Journal 292:660.

Dörje, F. et al., 1991, "Antagonist Binding Profiles of Five Cloned Human Muscarinic Receptor Subtypes", J. Pharmacology and Experimental Therapeutics 256:727–733.

Ebert, W., 1977, "Soft Elastic Gelatin Capsules: A Unique Dosage Form", Pharmaceutical Technology 1:44–50.

Goodman and Gilman's, 1996, *The Pharmacological Basis of Therapeutics*, 9th Ed. pp. 148, 588–592.

Herzog, A.R. et al., 1989, "Urinary Incontinence: Medical and Psychosocial Aspects", Annu. Rev. Gerontol. Geriatr. 9:74–119.

Hilbert, J. et al., 1987, "Pharmacokinetics and Dose Proportionality of Loratadine", J. Clin. Pharmacol. 27:694–698.

Knowles, S., 1992, "Astemizole and Terfenadine–Induced Cardiovascular Effects", Canadian J. Hospital Pharmacy 45:33–34.

Kohl and MacDonald, 1991, "New Pharmacologic Approaches to the Prevention of Space/Motion Sickness", J. Clin. Pharmacol. 31:934–946.

Kubo, N. et al., 1987, "Antimuscarinic Effects of Antihistamines: Quantitative Evaluation by Receptor–Binding Assay", Japan J. Pharmacol. 43:277–282.

Lathers, C. et al., 1989, "Pharmacology in Space", TiPS, 10:243–250.

Levin and Wein, 1982, "Direct Measurement of the Anticholinergic Activity of a Series of Pharmacological Compounds on the Canine and Rabbit Urinary Bladder", J. Urology 128:396–398.

Lunde, I., 1990, "Antihistamines", Side Effects of Drugs 14:135–138.

Massad, C. et al., 1992, "The Pharmokinetics of Intravesical and Oral Oxybutynin Chloride", J. Urology 148:595–597.

McCue, J., 1996, "Safety of Antihistamines in the Treatment of Allergic Rhinitis in Elderly Patients", Arch. Fam. Med. 5:464–468.

Mirakhur and Dundee, 1983, "Glycopyrrolate: Pharmacology and Clinical Use", Anaesthesia 38:1195–1204.

Mitchelson, F., 1992, "Pharmacological Agents Affecting Emesis", Drugs 43:443–463.

Muskat, Y. et al., 1996, "The Use of Scopolamine in the Treatment of Detrusor Instability", J. Urology 156:1989–1990.

Neiemans, F.A., 1988, "Antiallergic and Antitussive Drugs", Side Effects of Drugs 12:144–147.

Peggs and Shimp, 1995, "Antihistamines: The Old and The New", American Family Physician 52:593–600.

Quercia and Broisman, 1993, "Focus on Loratadine: A New Second–Generation Nonsedating $H_1$–Receptor Antagonist", Hosp. Formul. 28:137–153.

Resnick, N., 1995, "Urinary Incontinence", The Lancet 346:94–99.

Roman and Danzig, 1993, "Loratadine", Clinical Reviews in Allergy 11:89–110.

(List continued on next page.)

*Primary Examiner*—Minna Moezie
*Attorney, Agent, or Firm*—Pennie & Edmonds LLP

[57] ABSTRACT

Methods for treating urinary incontinence comprising administering a therapeutically effective amount of descarboethoxyloratadine, or a pharmaceutically acceptable salt thereof.

7 Claims, 1 Drawing Sheet

OTHER PUBLICATIONS

Simons, F.E.R. et al., 1988, "Astemizole–Induced Torsade de Pointes", The Lancet 2:624.

Simons, F.E.R., 1994, "$H_1$–Receptor Antagonists", Drug Safety 10:350–380.

Wein, A., 1995, "Pharmacology of Incontinence", Urol. Clin. N. Am. 22:557–577.

Wood, C., 1979, "Antimotion Sickness and Antiemetic Drugs", Drugs 17:471–479.

Yarker, Y. et al., 1995, "Oxybutynin", Drugs & Aging 6:243–262.

M.N.G. Dukes et al., "Side Effects of Drugs Annual 12," Elsevier Science Publishers B.V.: 142–143 (1988).

Petrin, A., 1974, "Motion Sickness and its Treatment", *Schweiz. Med.* 63:79–81.

Wood, C.D. et al., 1987, "Mechanisms of Antimotion Sickness Drugs", *Aviation, Space, and Envir. Med.* 58 (9, Suppl.) pp. A262–A265.

METHODS FOR TREATING URINARY INCONTINENCE USING DESCARBOETHOXYLORATADINE

FIELD OF THE INVENTION

The present invention relates to methods for treating urinary incontinence, vertigo and motion sickness.

BACKGROUND OF THE INVENTION

Urinary incontinence, such as incontinence caused by bladder detrusor muscle instability, is a prevalent problem that affects people of all ages and levels of physical health, both in healthcare settings and in the community at large. At present, urinary incontinence afflicts 15–30% of elderly people living at home, one-third of those living in acute-care settings, and at least one-half of those in long-term care institutions (Resnick, R. M., *Lancet* 346:94 (1995)). Medically, it predisposes persons to urinary tract infections, pressure ulcers, perineal rashes, and urosepsis. Psychosocially, urinary incontinence is associated with embarrassment, social stigmatization, depression, and with the risk of institutionalization (Herzo et al., *Annu. Rev. Gerontol. Geriatr.* 9:74 (1989)). Economically, the costs are great; in the United States alone, over $15 billion is spent per annum managing incontinence.

Treatments for incontinence include drugs with bladder relaxant properties, i.e., which help to control bladder detrusor muscle overactivity. Such drugs are effective in 80 to 85% of patients with uninhibited bladder contractions. Anticholinergic medications represent the mainstay of this type of treatment. The major proportion of the neurohumoral stimulus for physiologic bladder contraction is acetylcholine-induced stimulation of post ganglionic muscarinic receptor sites on bladder smooth muscle. For example, anticholinergics such as propantheline bromide and glycopyrrolate, and combination smooth muscle relaxant/anticholinergics such as racemic oxybutynin and dicyclomine, have been used to treat urge incontinence. (See, e.g., Wein, A. J., *Urol. Clin. N. Am.* 22:557–577 (1995); Levin et al., *J. Urol.* 128:396–398 (1982); Cooke et al., *S. Afr. Med. J.* 63:3 (1983); R. K. Mirakhur et al., *Anaesthesia* 38:1195–1204 (1983)).

However, none of the existing commercial drug treatments for incontinence has achieved complete success with all classes of incontinent patients, nor has treatment occurred without significant adverse (side) effects. For example, adverse effects, such as drowsiness, dry mouth, constipation, blurred vision, headaches, tachycardia, and cardiac arrhythmia which are related to the anticholinergic activity of such drugs, occur frequently and can be sufficiently troublesome to necessitate discontinuing treatment in up to 25% of patients, depending on the dosage. Yet, despite the occurrence of unwanted anticholinergic effects in many patients such drugs are currently prescribed for patients with bladder detrusor muscle hyperactivity when pharmacological therapy is indicated (Cf. Yarllur et al., *Drugs Aging* 6:243 (1995)).

The effects of acetylcholine are prevented when muscarinic receptor antagonists block its binding to muscarinic cholinergic receptors at certain neuroeffector sites such as in the urinary bladder (see Goodman & Gilman's, *The Pharmacological Basis of Therapeutics*, 9th Ed. p. 148 (1996)).

Scopolamine, a muscarinic antagonist, has been reported to be effective, when administered transdermally, in the treatment of detrusor instability in female patients (Muskat et al., *The Journal of Urology* 156:1989–1990 (1996)). Muskat et al. state that when the drug is administered by an oral or systemic route, it causes severe side-effects and also discuss the contradictory reports regarding the transdermal administration of scopolamine. Muskat et al. report that although scopolamine is known to cause cycloplegia and dryness of the mouth, the side-effects in its study were not so severe to require discontinuation of the medication (Id. at 1990). Scopolamine is also reported as being used widely for motion sickness and as effective for the treatment of vertigo (Id.). However, it has also been reported that scopolamine has unwanted sedative effects (see Lathers et al., *TIPS* 10:243–250 (1989)).

Certain first generation $H_1$-receptor antihistamines, such as diphenylpyraline and promethazine, have been reported as having significant affinity for the muscarinic receptors (Kubo et al., *Japan J. Pharmacol.* 43:277–282 (1987)). Some first generation $H_1$ receptor antihistamines, such as dimenhydrinate, cyclizine and meclizine, have also been found to be effective for treating either vertigo or motion sickness (Id; Wood, C., *Drugs* 17:471–479 (1979); Cohen et al., *Archives of Neurology* 27:129–135 (1972); see also Goodman & Gilman's, *The Pharmacological Basis of Therapeutics*, 9th Ed. p. 588, 592 (1996)).

Peggs et al. (*American Family Physician* 52(2):593–600 (1995)), note that classic antihistamines, which have a greater propensity to cross the blood-brain barrier, would appear to be better indicated for the treatment of these conditions. However, the first generation $H_1$ antihistamines have undesirable side-effects, such as sedation (see Goodman's & Gilman's, *The Pharmacological Basis of Therapeutics*, 9th Ed. p. 590 (1996).

The second generation $H_1$-receptor antihistamines, such as terfenadine, astemizole and loratadine, while having fewer sedative effects, are reported as having weak or no effect on muscarinic receptors (Goodman & Gilman's, *The Pharmacological Basis of Therapeutics*, 9th Ed. p. 588 (1996); Simons, F. E., *Drugs Safety* 10(5):350–380 (1994)). This is consistent with the findings that such compounds do not possess any significant anticholinergic affects (see Simons, F. E., *Drug Safety* 10(5):350–380 (1994); Roman et al., *Clinical Reviews in Allergy* 11:89–110 (1993)). Quercia et al. (*Hosp. Formul.* 28:137–153 (1993)) reported that loratadine does not exhibit substantial anticholinergic or alpha-adrenergic effects since it has only a weak affinity for alpha-adrenoreceptor and acetylcholine receptors.

Astemizole has been reported to alleviate chronic vertigo (see Mitchelson F., *Drugs* 43(4):443–463 (1992)). However, astemizole and terfenadine have also been reported as ineffective at preventing motion sickness (Cheung et al., *J. Clin. Pharmacol.* 32:163–175 (1992)). Kohl et al. (*J. Clin. Pharmacol.* 31:934–946 (1991)) reported moderate efficacy of a single 300 mg dose of terfenadine (which is five fold higher than the recommended single dose) for motion sickness and pronounced individual response differences.

Kubo et al. (*Japan J. Pharmacol.* 43:277–282 (1987)) state that the anti-motion sickness activity of some of the $H_1$ receptor antagonists may be related to their antimuscarinic ability. Kubo et al. also state that since histamine $H_1$ receptor blockade is suggested to be associated with the sedative activity, a drug which has both antimuscarinic and antihistaminic effects may be more effective in the treatment of motion sickness.

Clinical efficacy trials indicated that loratadine is an effective $H_1$ antagonist (see Clissold et al., *Drugs* 37:42–57 (1989)). Loratadine binds preferentially to peripheral rather than to central $H_1$ receptors (Quercia et al., *Hosp. Formul.* 28:137–153 (1993)).

Loratadine is well absorbed but is extensively metabolized (Hilbert, et al., *J. Clin. Pharmacol.* 27:694–98 (1987)). The main metabolite, descarboethoxyloratadine, which has been identified, is reported to be pharmacologically active (Clissold, *Drugs* 37:42[14] 57 (1989)). It is also reported as having antihistaminic activity in U.S. Pat. No. 4,659,716. This patent recommends an oral dosage range of 5 to 100 mg/day and preferably 10 to 20 mg/day.

As explained, supra, the second generation $H_1$ antagonists, such as loratadine, possess no or weak anticholinergic effects. Furthermore, astemizole and terfenadine, have been known to cause severe cardiac electrophysiologic adverse side-effects. These adverse side-effects are associated with a prolonged QT interval, and include, but are not limited to, ventricular fibrillation and cardiac arrhythmias, such as ventricular tachyarrhythmias or torsade de pointes. (Knowles, *Canadian Journal Hosp. Pharm.* 45:33,37 (1992); Craft, *British Medical Journal* 292:660 (1986); Simons et al., *Lancet,* 2:624 (1988); and Unknown, *Side Effects of Drugs Annual* 12:142 and 14:135). McCue, J. (*Arch. Fam. Med.* 5:464–468 (1996)) reports that loratadine does not appear to have adverse electrocardiographic effects.

Quercia et al. (*Hosp. Formul.* 28:137,142 (1993)) noted that serious cardiovascular adverse side-effects, including torsade de pointes and other ventricular arrhythmias, were reported in "healthy" patients who received terfenadine concurrently with either ketoconazole or erythromycin. Quercia et al. states that arrhythmias have also been reported with the concomitant administration of astemizole and erythromycin or erythromycin plus ketoconazole. Thus, he cautions against using loratadine concurrently with ketoconazole, itraconazole, and macrolides, such as erythromycin. McCue, J. (*Arch. Fam. Med.* 5:464–468 (1996)) reported that coadministration of loratadine with ketoconazole, erythromycin and cimetidine revealed no clinically relevant changes in cardiac repolarization or other electrocardiographic effects.

Additionally, it is known that ketoconazole, itraconazole, and/or erythromycin interfere with cytochrome P450, and thereby inhibit the metabolism of non-sedative antihistamines such as terfenadine, astemizole, and loratadine (see Andersen et al., *Arch. Dermatol.* 131:468–473 (1995)). Thus, there exists a potential for adverse interactions between loratadine and such drugs.

Brandes et al., (*Cancer Res.* (52):3796–3800 (1992)), showed that the propensity of drugs to promote tumor growth in vivo correlated with potency to inhibit concanavalin A stimulation of lymphocyte mitogenesis. Brandes et al., (*J. Nat'l Cancer Inst.* 86(10):771–775 (1994)), assessed loratadine in an in vitro assay to predict enhancement of in vivo tumor growth. This reference also reported that loratadine (at a dose of about 10 mg/day) and astemizole are associated with growth of both melanoma and fibrosarcoma tumors, in vivo.

Based upon the above discussion, it is clear that there is a need for an effective drug for the treatment of urinary incontinence, vertigo, and motion sickness which does not possess the adverse side-effects of the drugs previously prescribed for such disorders. There is also a need for a drug for the treatment of these conditions, which, in contrast to the second generation antihistamines, has anticholinergic activity, yet does not cause the adverse effects associated with administration of the first or second generation antihistamines.

SUMMARY OF THE INVENTION

The present invention provides methods for the effective treatment of urinary incontinence, vertigo and motion sickness based on the unexpected finding that a metabolite of loratadine, descarboethoxyloratadine ("DCL"), provides a superior treatment of urinary incontinence, and vestibular disorders, such as vertigo and motion sickness, than drugs previously associated with the treatment of such disorders.

The methods of the present invention comprise administering a therapeutically effective amount of DCL. Chemically, DCL is 8-chloro-6,11-dihydro-11-(4-piperidylidene)-5H-benzo[5,6]cyclohepta[1,2-b]pyridine, and has the following structure:

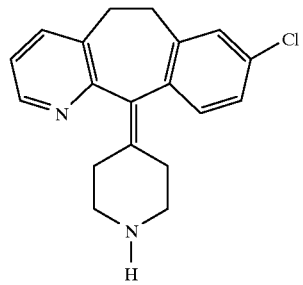

In one aspect the invention relates to a method for treating urinary incontinence which comprises administering to a human in need of such treatment a therapeutically effective amount of DCL or a pharmaceutically acceptable salt thereof.

In another aspect, the present invention provides a method for treating vertigo comprising administering to a human in need of such treatment a therapeutically effective amount of DCL or a pharmaceutically acceptable salt thereof.

In a further aspect, the present invention provides a method for treating motion sickness comprising administering to a human in need of such treatment a therapeutically effective amount of DCL or a pharmaceutically acceptable salt thereof.

In another aspect, DCL can be used in accordance with this invention to effectively treat urinary incontinence while substantially reducing or avoiding the adverse side-effects associated with existing drugs for the treatment of urinary incontinence such as scopolamine and racemic oxybutynin. DCL can also be used in accordance with this invention to effectively treat vertigo and motion sickness, including, but not limited to, space motion sickness (or space adaptation syndrome) and sea sickness, while substantially reducing the adverse side-effects that primarily arise from drugs that are associated with the treatment of vertigo and motion sickness, such as scopolamine and meclizine. The adverse effects include, but are not limited to, xerostomia, mydriasis, drowsiness, nausea, constipation, palpitations and tachycardia. DCL also has the additional therapeutic benefit of not causing side-effects associated with certain second generation antihistamines such as cardiac arrythmia, associated with astemizole and terfenadine, or the potential to promote tumors, associated with loratadine.

The present invention also encompasses compositions for use in the methods for treating motion sickness, comprising a therapeutically effective amount of DCL or a pharmaceutically acceptable salt thereof, a therapeutically effective amount of ephedrine, and a pharmaceutically acceptable carrier.

The present invention also encompasses compositions for use in the methods of the present invention for treating motion sickness, comprising a therapeutically effective amount of DCL or a pharmaceutically acceptable salt thereof, a therapeutically effective amount of a drug selected from the group consisting of amphetamines, amphetamine salts and amphetamine analogs, and a pharmacologically acceptable carrier.

The present invention also encompasses compositions for use in the methods for treating motion sickness, comprising a therapeutically effective amount of DCL or a pharmaceutically acceptable salt thereof, a therapeutically effective amount of an amphetamine agent, and a pharmaceutically acceptable carrier.

The present invention also encompasses compositions for use in the methods of the present invention for treating motion sickness, comprising a therapeutically effective amount of DCL or a pharmaceutically acceptable salt thereof, a therapeutically effective amount of a psychostimulant, and a pharmaceutically acceptable carrier.

In a further aspect, the present invention provides a method for treating motion sickness comprising administering to a human in need of such treatment a therapeutically effective amount of DCL or a pharmaceutically acceptable salt thereof and a therapeutically effective amount of a decongestant.

In a further aspect, the present invention provides a method for treating motion sickness comprising administering to a human in need of such treatment a therapeutically effective amount of DCL or a pharmaceutically acceptable salt thereof and a therapeutically effective amount of ephedrine.

Additionally, the present invention is directed to a method for treating motion sickness comprising administering to a human in need of such treatment a therapeutically effective amount of DCL or a pharmaceutically acceptable salt thereof and a therapeutically effective amount of a drug selected from the group consisting of amphetamines, amphetamine salts and amphetamine analogs.

The present invention is also directed to a method for treating motion sickness comprising administering to a human in need of such treatment a therapeutically effective amount of DCL or a pharmaceutically acceptable salt thereof and a therapeutically effective amount of an amphetamine agent.

In another aspect, the present invention provides a method for treating motion sickness, comprising administering to a human in need of such treatment a therapeutically effective amount of DCL or a pharmaceutically acceptable salt thereof and a therapeutically effective amount of a psychostimulant.

According to the present invention, DCL may be administered parenterally, rectally, intravesically, transdermally, orally, intravascularly, by inhalation, or by aerosol, at a rate of about 0.1 mg to about 100 mg per day. Oral and transdermal are the preferred routes for the treatment of vertigo and motion sickness. Oral, intravenous and intravesically are the preferred routes for the treatment of urinary incontinence at the same dosage range.

DETAILED DESCRIPTION OF THE INVENTION

Figure 1:
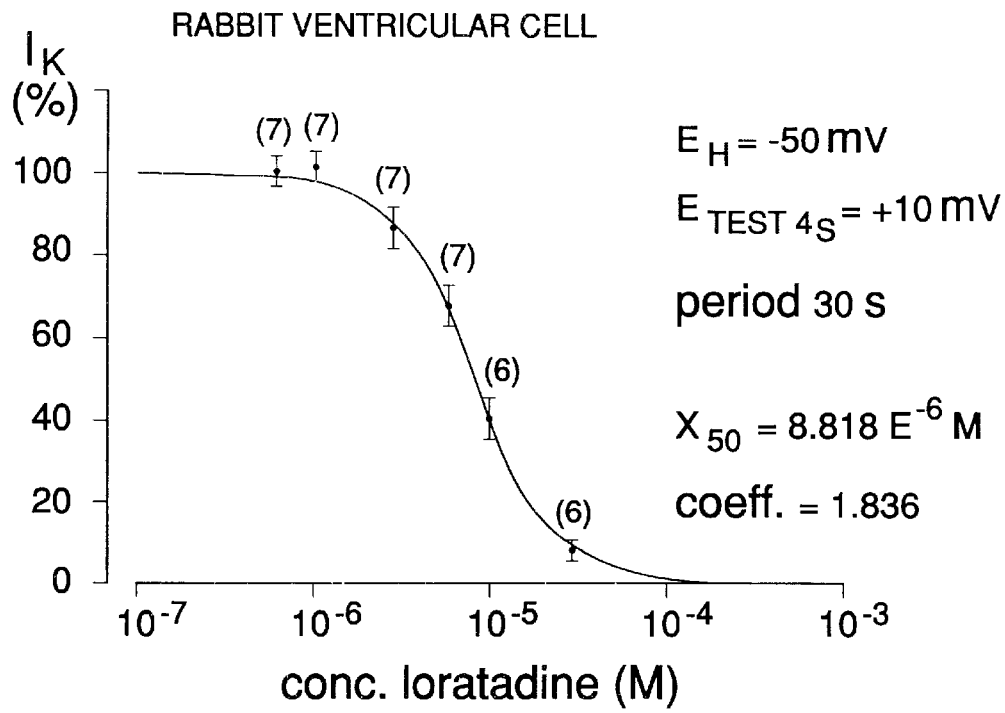
FIG. 1 represents the effect of loratadine on the delayed rectifying K$^+$ current ($I_{Kr}$) in rabbit ventricular myocytes.

The present invention encompasses a method for treating urinary incontinence which comprises administering to a human in need of such treatment a therapeutically effective amount of DCL, or a pharmaceutically acceptable salt thereof.

The present invention also encompasses a method for treating vertigo which comprises administering to a human in need of such treatment a therapeutically effective amount of DCL, or a pharmaceutically acceptable salt thereof.

Another embodiment of the present invention is a method of treating motion sickness which comprises administering to a human in need of such treatment, a therapeutically effective amount of DCL, or a pharmaceutically acceptable salt thereof. One advantage of using DCL to treat motion sickness is that it lacks sedative effects.

The present invention also relates to methods for treating urinary incontinence, vertigo and/or motion sickness while avoiding the adverse effects associated with existing drugs used to treat these indications.

The present invention also encompasses the use of DCL, or compositions containing DCL, to treat the above-described conditions while avoiding cardiac arrhythmias and tumor promotion. Thus, the present invention also relates to the use of DCL to treat such conditions in a human having a higher then normal propensity for or incidence of cancer.

The present invention also relates to methods of treating urinary incontinence, vertigo, motion sickness while avoiding adverse events associated with co-administration of a drug that inhibits cytochrome, P450, including, but not limited to, ketoconazole, itraconazole, erythromycin, and others known by those skilled in the art.

The present invention is also related to a method for treating urinary incontinence, vertigo and/or motion sickness in a patient having a higher than normal propensity for Long QT Syndrome as a result of either genetic and/or environmental factors.

The present invention also involves compositions having anticholinergic activity for use in such methods which comprise a therapeutically effective amount of DCL, or a pharmaceutically acceptable salt thereof, and a pharmaceutically acceptable carrier.

The present invention also encompasses compositions for use in the methods for treating motion sickness, comprising a therapeutically effective amount of DCL or a pharmaceutically acceptable salt thereof, a therapeutically effective amount of ephedrine, and a pharmaceutically acceptable carrier.

The present invention also encompasses compositions for use in the methods for treating motion sickness, comprising a therapeutically effective amount of DCL or a pharmaceutically acceptable salt thereof, a therapeutically effective amount of a drug selected from the group consisting of amphetamines, amphetamine salts, and amphetamine analogs, and a pharmaceutically acceptable carrier.

The present invention also encompasses compositions for use in the methods for treating motion sickness, comprising a therapeutically effective amount of DCL or a pharmaceutically acceptable salt thereof, a therapeutically effective amount of an amphetamine agent, and a pharmaceutically acceptable carrier.

The present invention also encompasses compositions for use in the methods for treating motion sickness, comprising a therapeutically effective amount of DCL or a pharmaceutically acceptable salt thereof, a therapeutically effective amount of a psychostimulant, including, but not limited to, pemoline and methylphenidate and a pharmaceutically acceptable carrier.

In a further aspect, the present invention provides a method for treating motion sickness comprising administering to a human in need of such treatment a therapeutically effective amount of DCL or a pharmaceutically acceptable salt thereof and a therapeutically effective amount of a decongestant such as, but not limited to, pseudoephedrine and phenylpropanolamine. The administration of DCL and decongestant in the methods of the present invention for treating motion sickness may be either concurrent or sequential, i.e., DCL and decongestant may be administered as a combination, concurrently but separately, or by the sequential administration of DCL and decongestant or the sequential administration of decongestant and DCL.

In a further aspect, the present invention provides a method for treating motion sickness comprising administering to a human in need of such treatment a therapeutically effective amount of DCL or a pharmaceutically acceptable salt thereof and a therapeutically effective amount of ephedrine. The administration of DCL and ephedrine in the methods of the present invention for treating motion sickness may be either concurrent or sequential, i.e., DCL and ephedrine may be administered as a combination, concurrently but separately, or by the sequential administration of DCL and ephedrine or the sequential administration of ephedrine and DCL.

In another aspect, the present invention provides a method for treating motion sickness comprising administering to a human in need of such treatment a therapeutically effective amount of DCL or a pharmaceutically acceptable salt thereof and a therapeutically effective amount of a drug selected from the group consisting of amphetamines, amphetamine salts, and amphetamine analogs. The administration of DCL and such a drug in the methods of the present invention for treating motion sickness may be either concurrent or sequential, i.e., DCL and the drug may be administered as a combination, concurrently but separately, or by the sequential administration of DCL and the drug or the sequential administration of the drug and DCL.

In a further embodiment, the present invention provides a method for treating motion sickness comprising administering to a human in need of such treatment a therapeutically effective amount of DCL or a pharmaceutically acceptable salt thereof and a therapeutically effective amount of an amphetamine agent. The administration of DCL and amphetamine agent in the methods of the present invention for treating motion sickness may be either concurrent or sequential, i.e., DCL and amphetamine agent may be administered as a combination, concurrently but separately, or by the sequential administration of DCL and amphetamine agent or the sequential administration of amphetamine agent and DCL.

In another embodiment, the present invention provides a method for treating motion sickness comprising administering to a human in need of such treatment a therapeutically effective amount of DCL or a pharmaceutically acceptable salt thereof, and a therapeutically effective amount of a psychostimulant, including, but not limited to, pemoline and methylphenidate. The administration of DCL and a psychostimulant in the methods of the present invention for treating motion sickness may be either concurrent or sequential, i.e., DCL and psychostimulant may be administered as a combination, concurrently but separately, or by the sequential administration of DCL and psychostimulant or the sequential administration of psychostimulant and DCL.

The term "adverse effects" as used herein, refers to the side-effects associated with administration of drugs used to treat urinary incontinence and/or vertigo and/or motion sickness, which are not part of the desired therapeutic effect of the drug. Such adverse effects, include, for illustrative purposes, drowsiness, epistaxis, xerostomia, mydriasis, cycloplegia, unstable cardiovascular status such as tachycardia and cardiac arrhythmia, increased ocular pressure, nausea, constipation, decreased sweating, impotence, and/or dermal manifestations such as urticaria.

The term "cardiac arrhythmias" includes, but is not limited to, Long QT Syndrome, ventricular tachyarrhythmias, torsade de pointes and ventricular fibrillation.

The term "epistaxis" refers to nosebleeds, e.g., hemorrhage from the nose. Epistaxis is a side effect of anticholinergics in children.

The term "xerostomia" refers to dryness of the mouth due to lack of normal secretion.

The term "mydriasis" refers to dilation of the pupil, and often results in blurred vision.

The term "cycloplegia" refers to paralysis of the ciliary muscle; paralysis of accommodation.

The term "urinary incontinence" means the inability to prevent the discharge of urinary excretions, and includes, but is not limited to, bladder detrusor muscle instability incontinence, stress incontinence, urge incontinence, overflow incontinence, enuresis, and post-prostectomy incontinence.

The term "enuresis" refers to the involuntary discharge of urine, and "nocturnal enuresis" refers to involuntary discharge of urine during sleep.

The term "vertigo" means an abnormal sensation of rotary movement associated with difficulty with balance, gait and navigation in the environment. The term also includes a disturbance in which the individual has a subjective impression of movement in space or of objects moving around the individual, usually with a loss of equilibrium. This results from a disturbance somewhere in the equilibratory apparatus: vestibule; semicircular canals, 8th nerve; vestibular nuclei in the brainstem and their temporal lobe connections; and eyes. This term includes, but is not limited to, vertigo which results from Meniere's disease.

The term "Meniere's Disease" means disorders characterized by recurring prostrating vertigo, sensory hearing loss, and tinnitus, associated with generalized dilation of the membranous labyrinth.

The term "motion sickness" means a disorder caused by repetitive angular and linear acceleration and deceleration and excessive stimulation of the vestibular apparatus by motion. The disorder is characterized primarily by nausea and vomiting. The term includes, but is not limited to space motion sickness, also referred to as space adaptation syndrome.

In accordance with the present invention, DCL can be used to treat urinary incontinence, vertigo and motion sickness by administration to a patient using any suitable route of administration. (See, *Remington: The Science and Practice of Pharmacy*, Nineteenth Edition, Chapters 83–95 (1995)). A preferred method of administration is oral administration. Another preferred route of administration is intravenous administration. A particularly preferred method of administration for the treatment of vertigo and motion sickness is transdermal administration.

According to the present invention, DCL is preferably administered as a pharmaceutical formulation (composition). The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts", refers to the relatively non-toxic, inorganic and organic salts of DCL. Representative salts include the bromide, chloride, hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulfonate salts and the like. (See, e.g., Berge et al., "Pharmaceutical Salts", *J. Pharm. Sci.* 66:1–19 (1977).)

Formulations of the present invention include those suitable for oral, nasal, topical (including buccal and sublingual), rectal, vaginal, parenteral (including subcutaneous, intramuscular, intravenous), intravascularly, intravesically, by aerosol and/or transdermal administration. Additionally, the drug may be administered directly into the bladder through the urethra, i.e., intravesically, as described by Massad et al., *J. Urol.* 148:595–597 (1992). The formulations may conveniently be presented in unit dosage form and may be prepared by any methods well known in the art of pharmacy. The amount of active ingredient which is combined with a carrier material to produce a single dosage form will vary depending upon the host being treated, and the particular mode of administration. The amount of active ingredient which may be combined with a carrier material to produce a single dosage form preferably will be that amount of DCL which produces a therapeutic effect. Generally, the amount of the active ingredient will range from about 1% to about 99% of the total formulation, preferably from about 5% to about 70%, and most preferably from about 10% to about 30%.

Methods of preparing these formulations or compositions include the step of bringing into association DCL with a pharmaceutically acceptable carrier and, optionally, one or more accessory ingredients. In general, the formulations are prepared by uniformly and intimately bringing into association DCL with liquid carriers, or finely divided solid carriers, or both, and any optional accessory ingredients, and then, if necessary, shaping the product.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the DCL from one organ, or portion of the body, to another organ or portion of the body. Each carrier must be "acceptable" in the sense of being compatible with the other ingredients of the formulation and not injurious to the patient.

Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations (see, *Remington: The Science and Practice of Pharmacy,* Nineteenth Edition, Chapter 80 (1995)).

Formulations of the present invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as a gelatin and glycerin, or sucrose and acacia), or as soft elastic gelatin capsules, and/or as mouth washes and the like, each containing a predetermined amount of a compound of the present invention as an active ingredient. DCL may also be administered as a bolus, electuary or paste.

In solid dosage forms of the present invention for oral administration (capsules, tablets, pills, dragees, powders, granules and the like), the active ingredient is mixed with one or more pharmaceutically acceptable carriers, such as sodium citrate or dicalcium phosphate, and/or may also be mixed with one or more of any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. In another embodiment, lactose-free compositions containing DCL are administered.

Release agents, coating agents, sweetening, flavoring and perfuming agents, preservatives and antioxidants can also be present in the compositions of the present invention. Examples of pharmaceutically acceptable antioxidants include: (1) water soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), and/or surface-active or dispersing agents. Molded tablets may be made by molding in a suitable machine a mixture of the powdered DCL moistened with an inert, liquid diluent.

The pharmaceutical compositions of the present invention may also be formulated in a soft elastic gelatin capsule unit dosage form by using conventional methods, well-known in the art (see, e.g., Ebert, *Pharm. Tech.* 1(5):44–50(1977)). Soft elastic gelatin capsules have a soft, globular, gelatin shell somewhat thicker than that of hard gelatin capsules, wherein a gelatin is plasticized by the addition of glycerin, sorbitol, or a similar polyol. The hardness of the capsule shell may be changed by varying the type of gelatin and the amounts of plasticizer and water. The soft gelatin shells may contain a preservative to prevent the growth of fungi, such as methyl- and propylparabens and sorbic acid. The active ingredient may be dissolved or suspended in a liquid vehicle or carrier, such as vegetable or mineral oils, glycols such as polyethylene glycol and propylene glycol, triglycerides, surfactants such as polysorbates, or a combination thereof.

The tablets, and other dosage forms of the pharmaceutical compositions of the present invention, such as dragees, capsules, pills and granules, may optionally be scored or prepared with coatings and shells, such as enteric coatings and other coatings well known in the pharmaceutical formulating art.

The pharmaceutical compositions of the present invention may also be formulated so as to provide slow or controlled release of the active ingredient therein using, for example, hydroxypropylmethyl cellulose in varying proportions to provide the desired release profile, other polymer matrices, liposomes and/or microspheres. They may also be administered by controlled release means and delivery devices such as those in U.S. Pat. Nos.: 3,845,770; 3,916,899; 3,536,809; 3,598,123; and 4,008,796; and PCT published application WO 92/20377.

The pharmaceutical compositions of the present invention may also optionally contain opacifying agents and may be formulated such that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of DCL include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions of the present invention can also include adjuvants such as wetting agents, emulsifying and suspending agents, sweetening, flavoring, coloring, perfuming and preservative agents.

Suspensions, in addition to the active DCL, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the present invention for rectal and vaginal administration may be presented as a suppository, which may be prepared by mixing one or more compounds of the invention with one or more suitable non-irritating excipients or carriers comprising, for example, cocoa butter, polyethylene glycol, a suppository wax or a salicylate. Such formulations of the present invention are solid at room temperature, but liquid at body temperature and, therefore, will melt in the rectum or vaginal cavity and release the active DCL.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of DCL include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

Formulations of the present invention in the form of ointments, pastes, creams and gels may contain, in addition to DCL, excipients, such as animal and vegetable fats, oils, waxes, paraffins, starch, tragacanth, cellulose derivatives, polyethylene glycols, silicones, bentonites, silicic acid, talc and/or zinc oxide, or mixtures thereof.

Powders and sprays may contain, in addition to DCL, excipients such as lactose, talc, silicic acid, aluminum hydroxide, calcium silicates and polyamide powder, or mixtures of these substances. Sprays may additionally contain customary propellants, such as, for example, chlorofluorohydrocarbons, volatile unsubstituted hydrocarbons, hydrocarbon ethers and compressed gases.

Transdermal patches have the added advantage of providing controlled delivery of the active DCL of the present invention to the body. Such dosage forms may be made by dissolving or dispersing the DCL in the proper medium. Absorption enhancers may also be used to increase the flux of the DCL across the skin. The rate of such flux can be controlled by either providing a rate controlling membrane or dispersing the DCL in a polymer matrix or gel.

Regardless of the route of administration selected, the pharmaceutical compositions of the present invention are formulated into pharmaceutically acceptable dosage forms by conventional methods known to those of skill in the art. Where necessary, the pharmaceutical compositions of the present invention are sterile or can be sterilized before administration to a patient.

In a preferred embodiment, the DCL compositions of the present invention are provided in tablet or capsule form. The capsules or tablets are preferably formulated with from about 0.1 mg to about 100 mg of DCL, more preferably with from about 0.5 mg to about 50 mg of DCL, and even more preferably with from about 1 mg to about 25 mg of DCL.

In another preferred embodiment, the DCL preparations of the present invention are provided in soft elastic gelatin capsule form. The soft elastic gelatin capsules are preferably formulated with from about 0.1 mg to about 100 mg of DCL, more preferably with from about 0.5 mg to about 50 mg of DCL, and even more preferably with from about 1 mg to about 25 mg of DCL.

Actual dosage levels of DCL in the pharmaceutical compositions of the present invention may be varied so as to obtain an amount of the active ingredient which is effective to achieve the desired therapeutic response for a particular patient, composition, and mode of administration, without being toxic to the patient.

The selected dosage level and frequency of administration will depend upon a variety of factors including the route of administration, the time of administration, the rate of excretion of the particular compound being employed, the duration of the treatment, other drugs, compounds and/or materials used in combination with the DCL, the age, sex, weight, condition, general health and prior medical history of the patient being treated, and like factors well known in the medical arts. For example, the dosage regimen is likely to vary with pregnant women, nursing mothers and children relative to healthy adults.

A physician having ordinary skill in the art can readily determine and prescribe the effective amount of the pharmaceutical composition required. For example, the physician could start doses of the compound employed in the pharmaceutical composition of the present invention at levels lower than that required in order to achieve the desired therapeutic effect and gradually increase the dosage until the desired effect is achieved.

A suitable daily dose of DCL will be that amount of the compound which is the lowest dose effective to produce a therapeutic effect. Such an effective dose will generally depend upon the factors described above. Generally, the total daily dose of DCL for the conditions described herein may be from about 0.1 mg to about 100 mg, more preferably from about 0.5 mg to about 50 mg, and more preferably from about 1 mg to about 25 mg. A suitable oral daily dose range of decongestant, ephedrine, amphetamines, amphetamine salts, amphetamine analogs, amphetamine agents or psychostimulant is from about 1 mg to about 300 mg. Further, a suitable oral daily dose of such agents can also be readily determined by those skilled in the art.

If desired, the effective daily dose of the active DCL may be administered as two or three sub-doses administered separately at appropriate intervals throughout the day, optionally, in unit dosage forms.

The invention is further illustrated by reference to the following examples, which are provided by way of illustration and not by way of limitation.

EXAMPLES

Example 1

Preparation of Loratadine and Its Metabolites

Loratadine can be synthesized, for example, by methods disclosed in U.S. Pat. No. 4,282,233. The metabolites are prepared similarly, by reaction steps conventional in the art, as described in U.S. Pat. No. 4,659,716 which is incorporated here by reference in its entirety. One common method of preparing DCL is to reflux loratadine in the presence of sodium hydroxide and ethanol as depicted below.

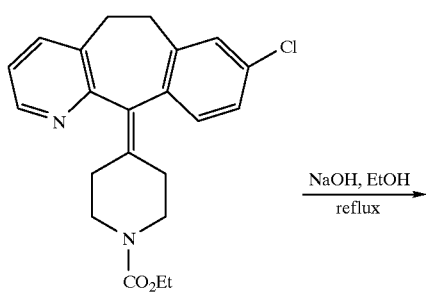

Claritin® or Loratadine

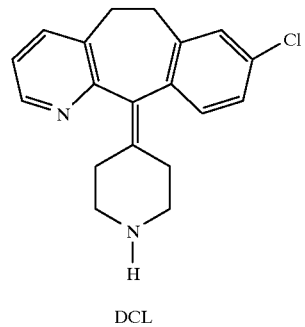

DCL

Extraction of Commercially Available Claritin® Tablets (600×10 ma)

Tablets of loratadine, were diluted with water and chloroform. The mixture was stirred, then filtered through celite, rinsed with chloroform until the filtrate contained no loratadine. The separated aqueous layer was extracted with chloroform twice. The combined organic layer was washed with water, brine and dried over sodium sulfate. The solvent was evaporated to give pure loratadine as a white solid.

Saponification of Loratadine

Loratadine (4.0 g) was added to a solution of sodium hydroxide (5.9 g) in 280 mL of absolute ethanol and the mixture was stirred at reflux for four days. The mixture was cooled and concentrated to remove ethanol. The residue was diluted with water and aqueous layer was extracted with methylene chloride five times. The combined organic layer was washed with water, brine and dried over sodium sulfate. The solvent was evaporated to give 2.82 g (87%) of pure loratadine derivative (or metabolite) as a pale-tan solid.

Example 2

Muscarinic Receptor Binding Studies

The aim of this study was to assess the affinity of six compounds for human $m_1$, $m_2$ and $m_3$ muscarinic receptor subtypes in radioligand binding assays. The method used herein is similar to that disclosed in Dörje et al. *The Journal of Pharmacology and Experimental Therapeutics* 256:2 727–733 (1991).

Methods

Samples were prepared and evaluated in a concentration range (0.1–3000 nM, half-log dilutions) on human recombinant $m_1$–$m_3$ receptors expressed in mammalian CHO cells. These data were generated from binding inhibition of radiolabelled ligand, where [$^3$H]pirenzepine was used for $m_1$, [$^3$H]AF-DX 384 was used for $m_2$, and [$^3$H]4-DAMP (4-diphenylacetoxy-N-methylpiperidine) was used for $m_3$.

Following incubation, the assays were rapidly filtered under vacuum through GF/B glass fiber filters (Packard) and washed with an ice-cold buffer using a Packard cell harvester. Bound radioactivity was determined with a liquid scintillation counter (Topcount, Packard) using a liquid scintillation cocktail (Microscint 0, Packard).

The compounds were tested on each receptor at (ten) 10 concentrations in duplicate to obtain competition curves. In each experiment, the reference compound for the receptor under investigation was simultaneously tested at (eight) 8 concentrations in duplicate to obtain a competition curve in order to validate this experiment. The parameters of this experiment are summarized in Table 1.

TABLE 1

| Receptor | Radioligand | Conc. | Non-specific | Incubation time/temp. | Reference Compound |
|---|---|---|---|---|---|
| $m_1$ | [$^3$H] pirenzepine | 2 nM | atropine (1 μM) | 60 min/ 25° C. | pirenzepine |
| $m_2$ | [$^3$H]AF-DX 384 | 3 nM | atropine (1 μM) | 60 min/ 25° C. | methontramine |
| $m_3$ | [$^3$H]A-DAMP | 0.15 nM | atropine (1 μM) | 60 min/ 25° C. | 4-DAMP |

The radioligands were from DuPont NEN; the cold ligands ere from Sigma or RBI. The drugs tested in this experiment were astemizole; norastemizole; loratadine; DCL, (S)(−) terfenadine carboxylate, and (S)(−) terfenadine.

Results

The specific radioligand binding to the receptors was defined as the difference between total binding and nonspecific binding determined in the presence of an excess of unlabelled ligand. Results were expressed as a percentage of control specific binding obtained in the presence of the compounds.

$IC_{50}$ values (concentration required to inhibit 50% of specific binding) and Hill coefficients (nH) were determined by non linear regression analysis of the competition curves. These parameters were obtained by Hill equation curve fitting using Sigmaplot™ software (Jandel).

The estimated $IC_{50}$ values (in nM) for the compounds tested and for the reference compounds at human $m_1$, $m_2$ and $m_3$ muscarinic receptor subtypes are indicated in Table 2.

TABLE 2

| | (estimated $IC_{50}$ values in nM) | | |
|---|---|---|---|
| | $m_1$ receptor | $m_2$ receptor | $m_3$ receptor |
| Astemizole | 900 | 1480 | 1210 |
| Norastemizole | 110 | 2380 | 1350 |
| (−) Terfenadine | >3000 | 3000 | >3000 |
| (S)(−) Terfenadine carboxylate | >3000 | >3000 | >3000 |
| Loratadine | >3000 | >3000 | >3000 |
| Descarboethoxy-loratadine | 85.0 | 50.4 | 755 |
| pirenzepine | 10.6 | not tested | not tested |
| methoctramine | not tested | 16.5 | not tested |
| 4-DAMP | not tested | not tested | 3.2 |

These results surprisingly show that DCL has a greater affinity at $m_1$, $m_2$, $m_3$ receptors than loratadine (the parent drug) or other second or third generation antihistamines. The present invention is based upon, inter alia, the surprising antimuscarinic affinity of DCL. Without being limited by theory, it is believed that the antimuscarinic affinity of DCL leads to its usefulness in the methods of treatment and compositions described herein.

Example 3

Tumor Promoting Activity

Inhibition of lymphocyte mitogenesis was used to screen the potencies of loratadine and DCL as tumor promoting agents.

Mitogenesis Studies

Fresh spleen cells ($5 \times 10^5$) obtained from 5-week old BALB/c mice (Charles River, ST. Constant, PQ) were suspended in RPMI 1640 medium containing 2% fetal calf serum (Grand Island Biological Co., Grand Island, N.Y.) and seeded into replicate microwell plates (Nunc) to which concanavalin (Con) A (2 μg/ml; Sigma Chemical Co., St. Louis, Mo.) was added. Cells were incubated (37° C., 95% air, 5% $CO_2$) in the absence or presence of increasing concentrations of the test agents dissolved in saline or other vehicles. Forty-three hours after the addition of Con A, 0.25 nmol $^3$H-thymidine (6.7 Ci/nmol; ICN Radiopharmaceuticals, Montreal, PQ) was added to each well. After an additional 5-hour incubation, the cells were washed from the wells onto filter papers employing an automated cell sorter. The filters were placed into vials containing 5 ml scintillation fluid (Readysafe; Beckman), and radioactivity incorporated into DNA at 48 hours was determined (n=3). $IC_{50}$ values for inhibition of mitogenesis were determined over wide range of concentrations (0.1 to 10 μM).

TABLE 3

| Inhibition of Concanavalin A Induced Stimulation of Lymphocytes ($IC_{50}$) | |
|---|---|
| Loratadine | 1.0 μM |
| DCL | 5.6 μM |

These results indicate that DCL is 5–7 fold less active than loratadine at promoting tumor growth.

Example 4

Cardiovascular Effects

The effects of DCL and loratadine on cardiac potassium currents were studied.

Methods

Single ventricular myocytes of the guinea-pig and the rabbit were dissociated by enzymatic dispersion (see Carmeliet, *J. Pharmacol. Exper. Ther.*, 1992, 262, 809–817 which is incorporated herein by reference in its entirety). The single suction patch electrode, with a resistance of 2 to 5 MΩ was used for voltage clamp (Axoclamp 200A). P-clamp software (Axon Instruments) was used to generate voltage-clamp protocols and to record and analyze data. The standard solution contained in mM: NaCl 137.6, KCl 5.4, $CaCl_2$ 1.8, $MgCl_2$ 0.5, HEPES 11.6 and glucose 5, and NaOH was added to pH 7.4. The intracellular solution contained: KCl 120, $MgCl_2$ 6, $CaCl_2$ 0.154, $Na_2ATP$ 5, EGTA 5, and HEPES 10, with KOH added until pH 7.2.

Figure 2:
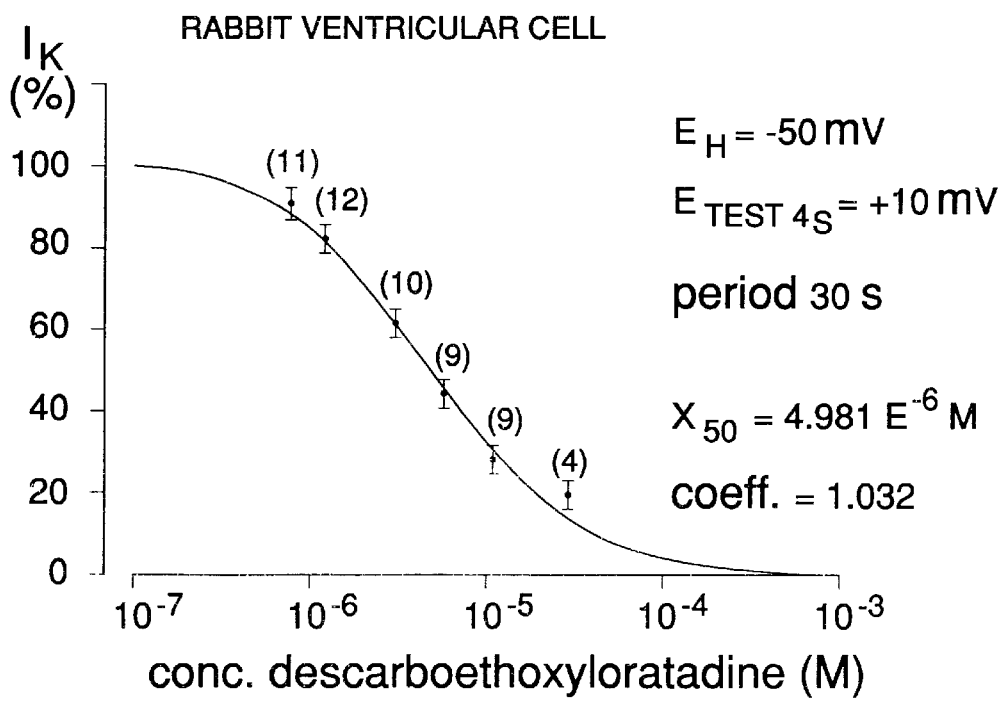
FIG. 2 represents the effect of DCL on the delayed rectifying K$^+$ current ($I_{Kr}$) in rabbit ventricular myocytes.

Effect on the Delayed Rectifying $K^+$ Current, ($I_{Kr}$) in Rabbit Ventricular Myocytes The voltage clamp protocol consisted of voltage steps from a holding potential of −50 mV to +10 mV for a duration of 4 sec. The change in tail current was measured as a function of the drug concentration. This concentration was changed between $10^{-7}$ and $10^{-5}$ M in five steps. Exposure to each concentration lasted 15 min. At the end, washout was attempted during 30 min. The results of this study are set forth in FIGS. 1 and 2 which indicate, respectively, that the $IC_{50}$ of loratadine is approximately $9 \times 10^{-6}$ M and the $IC_{50}$ of DCL is approximately $5 \times 10^{-6}$ M.

The results from this study indicate that DCL is less active than terfenadine in inhibiting the cardiac delayed rectifier and thus has no potential for cardiac side-effects at the daily dosages of the methods of the present invention. Thus, the methods of the present invention are less toxic than methods which use other non-sedating antihistamines.

Example 5

Inhibition of Cytochrome P450

This study was conducted to determine the extent that loratadine and DCL inhibit human cytochrome P4503A4 (CYP3A4). CYP3A4 is involved in many drug-drug interactions and quantitation of inhibition of CYP3A4 by loratadine or DCL provides an indication of the potential for the occurrence of adverse effects due to such drug-drug interactions. Inhibition was studied by measuring the metabolism of the model substrate testosterone by cDNA-derived human CYP3A4 in microsomes prepared from a human lymphoblastoid cell line designated h3A4v3.

Study Design

The inhibition study consisted of the determination of the 50% inhibitory concentration ($IC_{50}$) for the test substance. A single testosterone concentration (120 μM, approximately twice the apparent Km) and ten test substance concentrations, separated by approximately ½ log, were tested in duplicate. Testosterone metabolism was assayed by the production of the 6(β)-hydroxytestosterone metabolite. This metabolite was readily quantitated via HPLC separation with absorbance detection.

Storage/Preparation of the Test Substances and Addition to the Incubations

The test substances were stored at room temperature. The test substances were dissolved in ethanol for addition to the incubations. The addition of acid was not found to be needed. The solvent concentration was constant for all concentrations of the test substance.

$IC_{50}$ Determination

Final test substance concentrations were 100, 30, 10, 3, 1, 0.3, 0.1, 0.03, 0.01, 0.003 and 0 μM. Each test concentration was tested in duplicate incubations in accordance with the method below:

Method

A 0.5 ml reaction mixture containing 0.7 mg/ml protein, 1.3 mM NADP+, 3.3 mM glucose-6-phosphate, 0.4 U/ml glucose-6-phosphate dehydrogenase, 3.3 mM magnesium chloride and 120 μM testosterone in 100 mM potassium phosphate (pH 7.4) was incubated at 37° C. for 30 min. A known quantity of 11(β)-hydroxytestosterone was added as an internal standard to correct for recovery during extraction. The reaction mixture was extracted with 1 ml methylene chloride. The extract was dried over anhydrous magnesium sulfate and evaporated under vacuum. The sample was dissolved in methanol and injected into a 4.6×250 mm 5u C18 HPLC column and separated at 50° C. with a mobile phase methanol/water at a flow rate of 1 ml per min. The retention times were approximately 6 min for the 6(β)-hydroxy, 8 min for 11(β)-hydroxy and 12 min for testosterone. The product and internal standard were detected by their absorbance at 254 nm and quantitated by correcting for the extraction efficiency using the absorbance of the 11(β)-hydroxy peak and comparing to the absorbance of a standard curve for 6(β)-hydroxytestosterone.

Data Reporting

For each test substance concentration, the concentration of 6(β)-hydroxytestosterone metabolite in each replicate incubation was determined and the percentage inhibition relative to solvent control was calculated. The $IC_{50}$ was calculated by linear interpolation.

TABLE 4

| | Loratadine | |
| --- | --- | --- |
| Concentration (μM) | Pmole per Incubation | Percent Inhibition |
| 0 | 2692, 2108 | — |
| 0.003 | 1975, 2148 | 18, 11 |
| 0.01 | 2192, 1939 | 9, 19 |
| 0.03 | 1992, 2658 | 17, −11 |
| 0.1 | 2279, 2023 | 5, 16 |
| 0.3 | 2476, 2010 | −3, 16 |
| 1 | 2093, 1912 | 13, 20 |
| 3 | 2109, 1850 | 12, 23 |
| 10 | 1547, 1584 | 36, 34 |
| 30 | 1110, 1304 | 54, 46 |
| 100 | 643, 643 | 73, 73 |

The $IC_{50}$ for loratadine was calculated to be 30 μM.

TABLE 5

| | Descarboethoxyloratadine (DCL) | |
| --- | --- | --- |
| Concentration (μM) | Pmole per Incubation | Percent Inhibition |
| 0 | 1882, 2005 | — |
| 0.003 | 2010, 2053 | −3, −6 |
| 0.01 | 2100. 2151 | −8, −11 |
| 0.03 | 1950, 2261 | 0, −16 |
| 0.1 | 2111, 1966 | −9, −1 |
| 0.3 | 2055, 1959 | −6, −1 |
| 1 | 2029, 1982 | −4, −2 |
| 3 | 1748, 1948 | 10, 0 |
| 10 | 1478, 1557 | 24, 20 |
| 30 | 759, 671 | 61, 66 |
| 100 | 319, 225 | 84, 88 |

The $IC_{50}$ for DCL was calculated to be 23 μM.

This study demonstrates that there is little difference between the actions of loratadine and DCL on the inhibition of cytochrome P4503A4, and thus confirms that both do not themselves contribute to the potential for the occurrence of adverse effects due to drug-drug interactions.

Useful pharmaceutical dosage forms for administration of the compounds used in the methods of the present invention can be illustrated as follows:

Example 6

Soft Gelatin Capsules

A mixture of active ingredient in a digestible oil such as soybean oil, lecithin, cottonseed oil or olive oil is prepared and injected by means of a positive displacement pump into gelatin to form soft gelatin capsules containing 0.1 to 25 milligrams of the active ingredient. The capsules are washed and dried.

Example 7

Tablets

Compressed DCL tablets are prepared using conventional direct compression techniques, such that each dosage unit contains 0.1 mg to 25 mg of DCL. For example, tablets are prepared using 10 mg DCL, 80 mg microcrystalline cellulose, 5 mg stearic acid and 1 mg colloidal silica. All of the ingredients are blended in a suitable blender. The resulting mixture is compressed into tablets, using a 9/32-inch (7 mm) punch.

Tablets and capsules of other strengths may be prepared by altering the ratio of active ingredient to the excipients or to the final weight of the tablet.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference.

What is claimed is:

1. A method for treating urinary incontinence which comprises administering to a human in need of such treatment a therapeutically effective amount of descarboethoxyloratadine, or a pharmaceutically acceptable salt thereof.

2. The method according to claim 1, wherein the amount of descarboethoxyloratadine, or a pharmaceutically acceptable salt thereof, administered is from about 0.1 mg to about 100 mg per day.

3. The method according to claim 2, wherein the amount of descarboethoxyloratadine, or a pharmaceutically acceptable salt thereof, administered is from about 0.5 mg to about 50 mg per day.

4. The method according to claim 2, wherein descarboethoxyloratadine, or a pharmaceutically acceptable salt thereof, is administered by inhalation or by intravesical, parenteral, transdermal, rectal or oral administration.

5. The method according to claim 4, wherein descarboethoxyloratadine, or a pharmaceutically acceptable salt thereof, is administered by oral administration.

6. The method according to claim 4, wherein descarboethoxyloratadine, or a pharmaceutically acceptable salt thereof, is administered by transdermal administration.

7. The method according to claim 4, wherein descarboethoxyloratadine, or a pharmaceutically acceptable salt thereof, is administered by intravesical administration.

* * * * *